United States Patent [19]

Kurabayashi et al.

[11] Patent Number: 5,028,598

[45] Date of Patent: Jul. 2, 1991

[54] OXETANOCIN DERIVATIVES AND THEIR SALTS AS WELL AS USE THEREOF

[75] Inventors: Katsuhiko Kurabayashi, Annaka; Junichi Seki, Takasaki; Haruo Machida, Isesaki; Hiroshi Yoshikawa, Fujioka; Hiroo Hoshino, Maebashi; Seiichi Saito, Kashiwa; Masayuki Kitagawa, Urawa, all of Japan

[73] Assignee: Nippon Kayaku Kabushiki Kaisha, Tokyo, Japan

[21] Appl. No.: 573,466

[22] Filed: Aug. 27, 1990

[30] Foreign Application Priority Data

Sep. 8, 1989 [JP] Japan .................................. 1-231767
Jul. 12, 1990 [JP] Japan .................................. 2-182718

[51] Int. Cl.$^5$ ..................... A61K 31/53; C07F 9/06; C07D 487/04
[52] U.S. Cl. ..................................... 514/81; 514/243; 544/184
[58] Field of Search .................. 544/184; 514/243, 81

[56] References Cited

U.S. PATENT DOCUMENTS

| | | | |
|---|---|---|---|
| 3,917,583 | 11/1975 | Meyer et al. | 260/211.5 R |
| 4,728,736 | 3/1988 | Shealy et al. | 544/254 |
| 4,743,689 | 5/1988 | Shimada et al. | 544/277 |
| 4,845,215 | 7/1989 | Shimada et al. | 544/265 |
| 4,892,876 | 1/1990 | Hoshino et al. | 514/265 |

FOREIGN PATENT DOCUMENTS

| | | |
|---|---|---|
| 0291917 | 11/1988 | European Pat. Off. . |
| 0334250 | 9/1989 | European Pat. Off. . |
| 0335355 | 10/1989 | European Pat. Off. . |

OTHER PUBLICATIONS

The Journal of Medicinal Chemistry, 1972, vol. 15, No. 2, pp. 182-187.

*Primary Examiner*—Mary C. Lee
*Assistant Examiner*—Patricia L. Morris
*Attorney, Agent, or Firm*—Henry C. Nields

[57] ABSTRACT

Oxetanocin derivatives represented by formula:

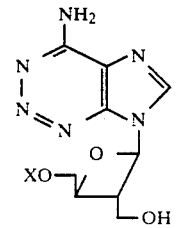

wherein X represents H or

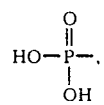

or a pharmacologically acceptable salt thereof exhibit an anti-viral activity. Anti-viral compositions comprising the oxetanocin derivatives or their pharmacologically acceptable salts as the effective ingredient are also provided.

4 Claims, No Drawings

OXETANOCIN DERIVATIVES AND THEIR SALTS AS WELL AS USE THEREOF

BACKGROUND OF THE INVENTION

1. Field of the Invention

The present invention relates to novel compounds having an antiviral activity and their use.

2. Prior Art Statement

It has been revealed that acquired immunodeficiency syndrome (hereafter referred to as AIDS) is a disease caused by human immunodeficiency virus (hereafter referred to as AIDS virus). For the treatment of AIDS, azidothymidine has been used but because of its side effects, a dose is limited and hence, a satisfactory therapeutic effect cannot be obtained.

Therefore, it has been desired to develop a novel anti-AIDS viral agent having a low toxicity.

SUMMARY OF THE INVENTION

As a result of various investigations, the present inventors have found that oxetanocin derivatives represented by formula (1):

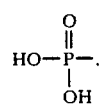
(1)

wherein X represents H or

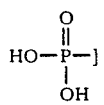

or pharmacologically acceptable salts thereof exhibit an anti-AIDS viral activity and can be the effective ingredient of anti-AIDS viral compositions. The present invention has thus been accomplished.

That is, the present invention provides:

(I) oxetanocin derivatives represented by formula (1) above or their pharmacologically acceptable salts; and, (II) anti-viral compositions comprising as the effective ingredient oxetanocin derivatives represented by formula (1) above or their pharmacologically acceptable salts.

DETAILED DESCRIPTION OF THE INVENTION

Among the compounds represented by formula (1), Compound (1H) shown by the following formula (1H) [in formula (1), X represents H] can be synthesized, using as a raw material Compound (2) represented by formula (2) [known oxetanocin A] (cf. Japanese Patent Application Laid-Open No. 61-293992), for example, via the following reaction route:

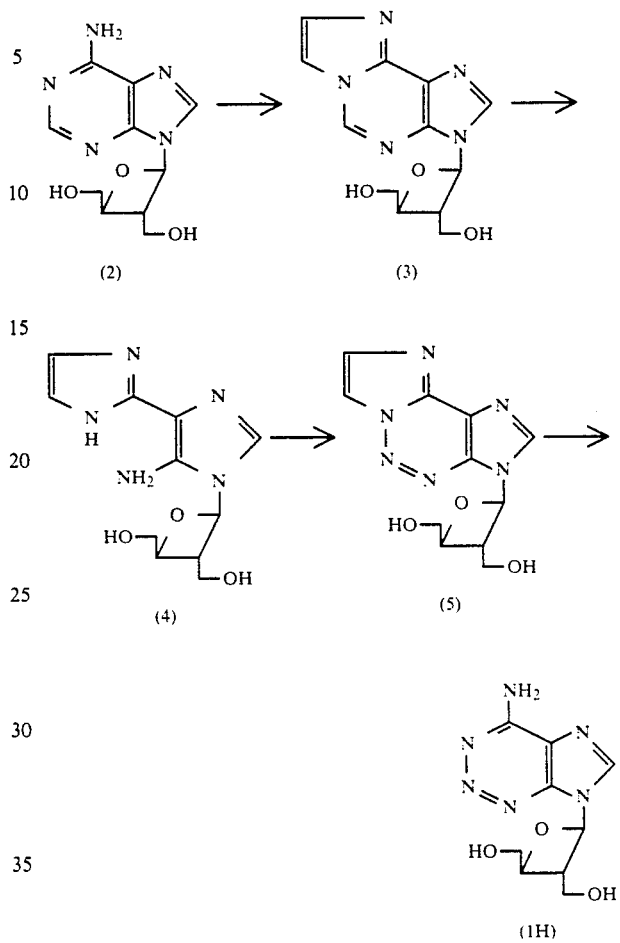

That is, Compound (2) is reacted with chloroacetaldehyde in the presence of sodium acetate and the resulting Compound (3) represented by formula (3) is then ring-opened with sodium hydroxide to give Compound (4) represented by formula (4). Next, Compound (4) is reacted with sodium nitrite in the presence of an acid to prepare Compound (5) represented by formula (5). Compound (5) is then reacted with N-bromosuccinimide to give Compound (1H).

Among the compounds (1) represented by formula (1), Compound (1P) shown by the following formula (1P) [in formula (1), X represents $$HO-\overset{O}{\underset{\underset{OH}{|}}{\overset{\|}{P}}}-]$$

can be synthesized, using as a raw material Compound (1H), for example, via the following reaction route:

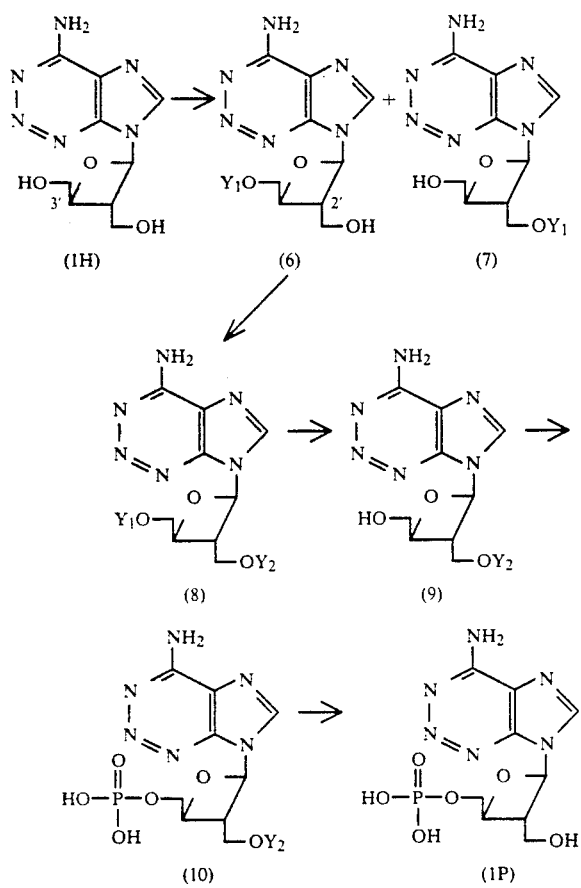

(wherein each of $Y_1$ and $Y_2$ independently represents a protective group which can be split off by different means).

That is, protective group $Y_1$ is introduced into the hydroxy group at the 3'—$CH_2OH$ in Compound (lH) to obtain Compound (6) represented by formula (6). In this case, Compound (7) represented by formula (7) is by-produced. Examples of protective group $Y_1$ include formyl or a lower alkylcarbonyl group which may optionally have a substituent (as the substituent, there are a halogen atom, a lower alkoxy, benzoyl, etc.), for example, acetyl, chloroacetyl, trichloroacetyl, methoxyacetyl, pivaloyl, phenoxyacetyl, trityloxyacetyl, etc.; an acyl group such as benzoyl, etc.; a lower alkyl group which may optionally have a substituent (for example, an unsubstituted lower alkyl such as t-butyl, etc., a substituted lower alkyl such as a substituted or unsubstituted trityl group, e.g., trityl or monomethoxytrityl, dimethoxytrityl, trimethoxytrityl, etc.); furthermore, a silyl group having various substituents (e.g., trimethylsilyl, t-butyldimethylsilyl, t-butyldiphenylsilyl, etc.); and the like. The protective group described above can be introduced by known methods and it is preferred to choose a protective group which can be efficiently split off upon removal of the protective group at a later stage. Compound (6) and Compound (7) can be separated from each other by column chromatography.

Next, protective group $Y_2$ is introduced into the hydroxy group at the 2'—$CH_2OH$ in Compound (6) to obtain Compound (8) represented by formula (8). As protective group $Y_2$, there is no particular restriction so long as the protective group can be removed by a different means from that used for removing protective group $Y_1$. In the case that protective group $Y_1$ is a silyl group having various substituents, an acyl group or, benzyl or allyl which can be removed by reduction may be used as protective group $Y_2$. In the case that protective group $Y_1$ is an acyl group, the above protective groups which can be removed by reduction may be used as protective group $Y_2$. The protective group can be introduced by known methods.

Then, the protective group $Y_1$ of Compound (8) is removed to obtain Compound (9) represented by formula (9). The protective group $Y_1$ can be removed in a conventional manner. For example, in the case that protective group $Y_1$ is a silyl group having various substituents, n-tetrabutylammonium fluoride may be used in tetrahydrofuran.

Thereafter, Compound (9) is phosphorylated with a phosphoric acid to give Compound (10) represented by formula (10). Phosphorylation can be performed in a conventional manner. As the phosphoric acid used for phosphorylation, phosphorus oxychloride or the like may be used. The reaction is generally carried out in the presence of a tri-lower alkyl phosphoric acid.

Lastly, protective group $Y_2$ of Compound (10) is removed to give Compound (lP). The removal of protective group $Y_2$ can be performed in a conventional manner. In the case that protective group $Y_2$ is, for example, benzyl which can be removed by reduction, the protective group $Y_2$ is removed generally by catalytic reduction using palladium-carbon, etc. Further in the case that the protective group $Y_2$ is an acyl group, the protective group $Y_2$ is removed using sodium methoxide or ammonia water.

Compound (lH) may be reacted with acids to form salts, thereby to convert into its pharmacologically acceptable salts. As the acid for forming the salts, any acid known to be pharmacologically acceptable may be used. Preferred examples of the acid include hydrochloric acid, sulfuric acid, phosphoric acid, etc. The salts may be obtained by mixing Compound (lH) with the acid in a conventional manner.

Compound (lP) may also be converted into its pharmacologically acceptable salts. Examples of the salts include ammonium salt, sodium salt, potassium salt, triethylamine salt, etc. Compound (lP) can be converted into the salts by mixing the compound with a base in a conventional manner.

The thus obtained compounds (1) (including the salts thereof, hereafter the same) exhibit an anti-AIDS viral activity as will be later described and are thus extremely useful as anti-AIDS viral agents. In the case that the compounds of the present invention are used as anti-AIDS viral agents, various known methods are applicable to the production of their pharmaceutical preparations and to their administration. That is, the compounds of the present invention may be administered by injection or through oral or rectal route. For pharmaceutical preparations, the compounds of the present invention may be prepared in the form of injections, powders, granules, tablets, suppositories, or the like.

In preparing the pharmaceutical preparations, there may be used various auxiliary agents used for medicines, namely, carriers or other aids, for example, stabilizers, preservatives, pain-free agents, emulsifiers or the like, if necessary and desired. A content of the compounds (I) may be varied over a wide range depending upon the form of preparations. However, the preparation contains Compound (1) in an amount of, generally 0.01 to 100% by weight, preferably 0.1 to 70% by weight. The preparation may contain, beside Compound (1), the auxiliary agents generally used for medicines such as carrier and the like. A dose of the compound of the present invention to be administered may vary depending upon condition of patients, etc. but is generally in the range of approximately 0.01 to 800 mg/day for an adult. Where consecutive administration is required, it is preferred to reduce the dose.

In general, the compounds (1) are used in the form of pharmaceutically acceptable salts, in producing the preparations.

The compounds of the present invention have low toxicity. Even though the compounds of the present invention are intraperitoneally administered to mouse in a single dose of 800 mg/kg, any toxic sign was not noted.

Next, the anti-AIDS viral activity and cytotoxicity of the compounds (1) of the present invention are explained below in more detail, by referring to a test example.

Test Example

After 0.5 ml of cell suspension prepared from MT-4 cells in $1 \times 10^5$/ml was charged in a 24 well tray, 50 μl of a solution containing a predetermined quantity of Compound (lH) or Compound (lP) was added to the suspension. After culturing at 37° C. for 2 hours in 5% (v/v) carbon dioxide incubator, $10^3$ to $10^4$ infection units of AIDS virus were added and cultured for 4 days. Then, a part of the culture medium was applied onto a slide glass and immobilized with acetone, after which development of virus antigen was observed by indirect fluorescent antibody method. As the primary antibody of the fluorescent antibody method, a serum of AIDS patient was used. As its secondary antibody, FITC-labelled anti-human IgG antibody was used.

Based on a proportion of the infected cells and non-infected cells where the chemical was added and where no chemical was added, a rate of infection was calculated. A concentration of the chemical and the rate of infection were plotted on semilogarithmic paper to determine 50% infection inhibitory concentration ($EC_{50}$ value).

Furthermore, cytotoxicity of Compound (lH) and Compound (lP) against MT-4 cells was examined without adding virus. After staining with Trypane Blue, viable cells were counted. Based on the count of viable cells where the chemical was added and where no chemical was added, a degree of inhibition was calculated. A concentration of the chemical and the degree of inhibition were plotted on semilogarithmic paper to determine 50% cytotoxicity ($CC_{50}$ value).

| Anti-AIDS Viral Activity and Cytotoxicity of Compound (1H) and Compound (1P) | | |
|---|---|---|
| | $EC_{50}$ (μg/ml) | $CC_{50}$ (μg/ml) |
| Compound (1H) | 0.035 | >100 |
| Compound (1P) | 0.14 | >100 |

As is clear from the test example described above, the compounds of the present invention markedly inhibit AIDS virus antigen in an extremely low concentration. In addition, the cytotoxicity is extremely weak. Therefore, the compounds of the present invention are expected to be new drugs for the treatment of AIDS.

Hereafter the present invention is specifically described with reference to the examples below but is not deemed to be limited to these examples.

EXAMPLE 1

Synthesis of Compound (3)

After 2 g of Compound (2) [oxetanocin A], 1 g of sodium acetate and 3 ml of 40% chloroacetaldehyde aqueous solution were added to 16 ml of water, the mixture was stirred at 60° C. for 4 hours. After completion of the reaction, saturated sodium hydrogencarbonate aqueous solution was added to neutralize the reaction mixture. After passing through a column of DIAION HP20 (300 ml) [produced by Mitsubishi Kasei Corporation], the column was washed with water followed by elution with 30% methanol aqueous solution. After the eluate was concentrated to dryness, the residue was recrystallized from ethanol to give 2 g of Compound (3). Physicochemical properties of Compound (3) are as follows.

m.p. 188°–189° C.

IR (KBr, cm$^{-1}$) 3425, 3300, 3130, 3100, 2915, 1640, 1495, 1335, 1180, 1090, 980, 845.

NMR (DMSO-d$_6$, ppm) 9.32 (s, lH), 8.86 (s, lH), 8.09 (d, lH), 7.57 (d, lH), 6.57 (d, lH), 5.28 (t, lH), 5.08 (t, lH), 4.59 (m, lH), 3.8–3.6 (m, 5H).

MS (FAB) 276 (M+H)$^+$, 160.

Synthesis of Compound (4)

To 20 ml of 0.4 N sodium hydroxide aqueous solution was added 1 g of Compound (3). After stirring at room temperature for 8 hours, acetic acid was added to the reaction solution to neutralize. The reaction solution was passed through a column of DIAION HP20 (300 ml), the column was washed with water followed by elution with 20% methanol aqueous solution. After the eluate was concentrated to dryness, the residue was recrystallized from ethanol to give 0.7 g of Compound (4). Physicochemical properties of Compound (4) are as follows.

m.p. 176°–178° C.

IR (KBr, cm$^{-1}$) 3420, 3270, 3190, 3175, 2920, 1640, 1620, 1578, 1325, 1105, 1030, 860, 715.

NMR (DMSO-d$_6$, ppm) 7.69 (s, lH), 6.88 (s, 2H), 5.98 (d, lH), 5.74 (s, 2H), 5.32 (br. s, lH), 4.97 (br. s, lH), 4.43 (m, lH), 3.7–3.4 (m, 5H).

MS (FAB) 266 (M+H)$^+$, 150

Synthesis of Compound (5)

After 0.53 g of Compound (4) was dissolved in 10 ml of 50% acetic acid aqueous solution, 0.16 g of sodium nitrite was added to the solution under ice-cooling. The mixture was stirred for an hour. After completion of the reaction, saturated sodium hydrogencarbonate aqueous solution was added to neutralize the reaction mixture. After passing through a column of DIAION HP20 (200 ml), the column was washed with water followed by elution with 30% methanol aqueous solution. After the eluate was concentrated to dryness, the residue was recrystallized from ethanol to give 0.4 g of Compound (5). Physicochemical properties of Compound (5) are as follows.

m.p. 200°–202° C.

IR (KBr, cm$^{-1}$) 3425, 3300, 3130, 3100, 2915, 1640, 1495, 1335, 1240, 1180, 1090, 980, 845.

NMR (DMSO-d₆, ppm) 9.25 (s, 1H), 8.79 (d, 1H), 7.88 (d, 1H), 6.79 (d, 1H), 5.31 (t, 1H), 5.14 (t, 1H), 4.69 (m, 1H), 3.8–3.7 (m, 5H).

MS (FAB) 277 (M+H)+, 161.

Synthesis of Compound (1H)

After 0.28 g of Compound (5) was dissolved in 20 ml of 1 M acetate buffer (pH 5.0), 0.89 g of N-bromosuccinimide was added to the solution. The mixture was stirred at room temperature overnight. After completion of the reaction, saturated sodium hydrogencarbonate aqueous solution was added to neutralize the reaction mixture. After passing through a column of DIAION HP20 (100 ml), the column was washed with water followed by elution with 10% methanol aqueous solution. After the eluate was concentrated to dryness, the residue was recrystallized from ethanol to give 0.13 g of Compound (1H).

Physicochemical properties of Compound (1H) are as follows.

m.p. 225°–226° C.

IR (KBr, cm⁻¹) 3450 (sh), 3330, 3170, 3100, 2930, 1685, 1670, 1655, 1610, 1440, 1220, 1120, 840.

NMR (DMSO-d₆, ppm) 8.94 (s, 1H), 7.86 (s, 2H), 6.59 (d, 1H), 5.31 (t, 1H), 5.07 (t, 1H), 4.61 (m, 1H), 3.8–3.6 (m, 5H).

MS (FAB) 253 (M+H)+, 137.

EXAMPLE 2

Synthesis of Compound (6)

After 1,163 mg of imidazole and further a solution of 1,170 mg of tert-butyldimethylsilyl chloride in 5 ml of anhydrous dimethylformamide were added to a solution of 1,969 mg of Compound (1H) in 25 ml of anhydrous dimethylformamide, the mixture was stirred at room temperature for 2 hours. The solvent was distilled off under reduced pressure and 50 ml of water was added to the residue followed by extraction 3 times with 50 ml of chloroform. After washing with saturated sodium chloride aqueous solution, the chloroform extract was dried over anhydrous sodium sulfate. Sodium sulfate was filtered off and the solvent was distilled off under reduced pressure to give light yellow syrup. The syrup was passed through a column packed with 150 g of silica gel and the column was eluted with chloroform-methanol (20 : 1). Fractions showing Rf value of about 0.35 in silica gel TLC [developing solvent: chloroform-methanol (10 : 1)] were collected and the solvent was distilled off under reduced pressure to give 554 mg of Compound (6). Furthermore, fractions showing Rf value of about 0.28 were collected and the solvent was distilled off under reduced pressure to give 484 mg of Compound (7).

Synthesis of Compound (8)

After 18 mg of 4-dimethylaminopyridine, 250 μl of acetic anhydride and 220 μl of triethylamine were added to a solution of 554 mg of Compound (6) in 55 ml of anhydrous chloroform, the mixture was stirred at room temperature for 30 minutes. To the reaction solution was added 30 ml of water. After fractionation, the chloroform layer was washed with saturated sodium chloride aqueous solution and then dried over anhydrous sodium sulfate. Sodium sulfate was filtered off and the solvent was distilled off under reduced pressure to give the colorless residue. The residue was passed through a column packed with 20 g of silica gel and the column was eluted with chloroform-methanol (20 : 1). Fractions showing Rf value of about 0.47 in silica gel TLC [developing solvent: chloroform-methanol (10 : 1)] were collected and the solvent was distilled off under reduced pressure to give 639 mg of Compound (8).

The results of NMR measurement of Compound (8) are as follows.

NMR (CDCl₃, ppm): 8.85 (1H, s, 8-H), 6.89 (2H, broad, s, NH₂), 6.79 (1H, d, J=5.82Hz, 1'—H), 4.78 (1H, m, 3'—H), 4.43 (2H, dd, J=5.82Hz, 12.05Hz, 2'—CH₂—), 3.78—4.18 (3H, m, 2'—H, 3'—CH₂—), 2.11

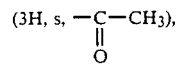

0.95 (9H, s), 0.18 (3H, s), 0.15 (3H, s).

Synthesis of Compound (9)

After 2.1 ml of 1.05 M solution of tetrabutylammonium fluoride in tetrahydrofuran was added to a solution of 639 mg of Compound (8) in 8 ml of tetrahydrofuran, the mixture was stirred at room temperature. The reaction solution was concentrated to dryness under reduced pressure to give the residue. The residue was passed through a column packed with 50 g of silica gel and the column was eluted with chloroform-methanol (10:1). The desired fractions were collected and the solvent was distilled off under reduced pressure to give 401 mg of Compound (9).

Synthesis of Compound (10)

After 0.42 ml of phosphorus oxychloride was added to a suspension of 400 mg of Compound (9) in 8.4 ml of triethyl phosphate in a nitrogen flow under cooling at −20° C., the mixture was stirred at 0° C. for 18 hours. Then, the reaction solution was added to 16 ml of saturated sodium carbonate aqueous solution followed by extraction 3 times with 20 ml of chloroform. After 150 ml of water was added to the aquoeus layer, the mixture was passed through 100 ml of DEAE-Sephadex A-25 (carbonate type) [produced by Pharmacin Fine Chemicals]. Elution was performed by linear gradient with 300 ml each of 0.1 M to 0.4 M triethylamine carbonate buffer (pH 7.4). Fractions showing Rf value of about 0.34 in silica gel TLC [developing solvent: n-butanol : acetic acid : water (12 : 3 : 5)] were collected and the solvent was distilled off under reduced pressure to give 750 mg of a mixture of Compound (10) and triethylamine carbonate.

Synthesis of Compound (1P)

After 750 mg of the mixture of Compound (10) and triethylamine carbonate was dissolved in 3.8 ml of water, pH of the solution was adjusted to 11.0 with 1 N sodium hydroxide solution. After stirring at room temperature for 8 hours, pH was adjusted to 1.8 with 1 N hydrochloric acid under ice-cooling. The solution was passed through a column packed with 10 ml of activated carbon. After washing with water, elution was performed with 80% methanol aqueous solution.

After pH of the eluate was adjusted to 6.85 with 1 N sodium hydroxide under ice cooling, the solvent was distilled off to give 380 mg of Compound (1P) disodium salt.

The results of NMR measurement and Rf value of Compound (IP) are as follows.

NMR (D$_2$O, ppm): 8.99 (1H, s, 8—H), 6.63 (1H, d, J=5.05Hz, 1'—H), 4.88 (1H, m, 2'—H), 4.09 (2H, m, 3'—CH$_2$—), 3.77–3.96 (3H, m). TLC (SiO$_2$): (2-propanol : conc. ammonia water : water=7:1:2), Rf 0.26.

What is claimed is:

1. An oxetanocin derivative represented by formula:

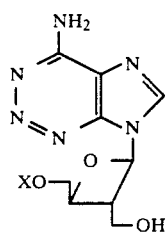

wherein X represents H or

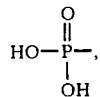

or a pharmacologically acceptable salt thereof.

2. An oxetanocin derivative or a pharmacologically acceptable salt thereof as claimed in claim 1, wherein X is H.

3. An oxetanocin derivative or a pharmacologically acceptable salt thereof as claimed in claim 1, wherein

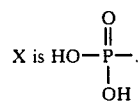

4. An anti-viral composition comprising as an effective ingredient an oxetanocin derivative or a pharmacologically acceptable salt thereof as claimed in claim 1, 2 or 3.

* * * * *